United States Patent
Hasjim et al.

(10) Patent No.: US 12,398,175 B2
(45) Date of Patent: Aug. 26, 2025

(54) METHOD FOR EXTRACTING PROTEIN, STARCH AND FIBER FROM BUCKWHEAT

(71) Applicant: ROQUETTE FRERES, Lestrem (FR)

(72) Inventors: Jovin Hasjim, Shanghai (CN); Jingling Tao, Shanghai (CN); Bernard Pora, Shanghai (CN)

(73) Assignee: Roquette Freres, Lestrem (FR)

( * ) Notice: Subject to any disclaimer, the term of this patent is extended or adjusted under 35 U.S.C. 154(b) by 704 days.

(21) Appl. No.: 16/611,050

(22) PCT Filed: May 14, 2018

(86) PCT No.: PCT/EP2018/062397
§ 371 (c)(1),
(2) Date: Nov. 5, 2019

(87) PCT Pub. No.: WO2018/210760
PCT Pub. Date: Nov. 22, 2018

(65) Prior Publication Data
US 2021/0284683 A1  Sep. 16, 2021

(30) Foreign Application Priority Data

May 16, 2017 (CN) .......................... 201710343271.0

(51) Int. Cl.
| | |
|---|---|
| *C08B 30/04* | (2006.01) |
| *C07K 1/14* | (2006.01) |
| *C07K 1/30* | (2006.01) |
| *C08B 30/02* | (2006.01) |
| *C08B 30/06* | (2006.01) |

(52) U.S. Cl.
CPC ............... *C07K 1/145* (2013.01); *C07K 1/30* (2013.01); *C08B 30/02* (2013.01); *C08B 30/04* (2013.01); *C08B 30/042* (2013.01); *C08B 30/046* (2013.01); *C08B 30/06* (2013.01)

(58) Field of Classification Search
CPC .......... C07K 1/145; C07K 1/30; C08B 30/02; C08B 30/04; C08B 30/042; C08B 30/046; C08B 30/06
See application file for complete search history.

(56) References Cited

U.S. PATENT DOCUMENTS 4,028,468 A   6/1977 Hohner et al.
4,171,384 A   10/1979 Chwalek et al.

FOREIGN PATENT DOCUMENTS

| CN | 1502633 A | * 11/2002 |
|---|---|---|
| CN | 1563094 A | 1/2005 |
| CN | 1654479 A | 8/2005 |
| CN | 101121756 A | 2/2008 |

OTHER PUBLICATIONS

Steadman, Buckwheat Seed Milling Fractions: Description, Macronutrient Composition and Dietary Fibre, Journal of Cereal Science 33 (2001) 271-278 (Year: 2001).*
Guo, Comparison of milling fractions of tartary buckwheat for their phenolics and antioxidant properties, Food Research International, vol. 49, Issue 1, Nov. 2012, pp. 53-59 (Year: 2012).*
Zheng et al. Food Research International, vol. 30, No. I, pp. 493-502, 1998.*
The English translation of the Brazilian Office Action, mailed on Jul. 19, 2022, in the related Brazilian Patent Appl. No. BR112019024112-4.
Li et al., "Physicochemical Properties of Common and Tartary Buckwheat Starch," Cereal Chem., vol. 74, No. 1, Jan./Feb. 1997, pp. 79-82.
Kurinami et al., "Physicochemical Properties of Common Buckwheat (*Fagopyrum esculentum* Moench) Starches," J. Appl. Glycosci., 2008, vol. 55, No. 2, J. pp. 95-99. (English abstract included.).
Agriculture and Livestock Industries Promotion Organization, "How "starch" is made," Oct. 4, 2012.
The English translation of the Chinese Office Action, mailed on Aug. 30, 2022, in the related Chinese Patent Appl. No. 201880032163. 4.
Chen et al., "Research on preparation process and processing properties of buckwheat starch," Food and Oil, vol. 29, No. 5, pp. 16-20, May 10, 2016. (The English abstract included.).
Liu et al., "Study on the Preparation Process and Properties of Tartary Buckwheat Starch," Chinese Journal of Food Science, vol. 13, No. 4, pp. 43-49, Apr. 30, 2013. (The English abstract included.).
Zhou et al., "Study on gelatinization characteristics of buckwheat starch", Food Science, vol. 30, No. 13, pp. 48-51, Jul. 1, 2009. (The English abstract included.).
The international Search Report and Written Opinion, mailed on Aug. 2, 2018, in the corresponding PCT Appl. No. PCT/EP2018/062397.
Li et al., "Correlation Between Dietary Fiber Content and the Environment in Different Tartary Buckwheat Cultivar," Hubei Agricultural Sciences, vol. 52, No. 22, pp. 5427-5433, Nov. 2013. (The English abstract included.).
The English translation of the Russian Office Action, mailed on Mar. 28, 2022, in the related Russian Patent Appl. No. 2019141297.

* cited by examiner

*Primary Examiner* — Jeanette M Lieb

(57) ABSTRACT

The present invention relates to a method for extracting protein, starch and fibers from buckwheat, more particularly from buckwheat groat or flour.

10 Claims, No Drawings

METHOD FOR EXTRACTING PROTEIN, STARCH AND FIBER FROM BUCKWHEAT

CROSS-REFERENCE TO RELATED APPLICATIONS

This application is a National Stage Application of PCT/EP2018/062397 filed May 14, 2018, which claims priority from Chinese Patent Application No. 201710343271.0, filed on May 16, 2017. The priority of said PCT and Chinese Patent Application are claimed. Each of the prior mentioned applications is hereby incorporated by reference herein in its entirety.

FIELD OF THE INVENTION

The invention relates to a method for extracting protein, starch and fibers from buckwheat, more particularly from buckwheat groat or flour.

BACKGROUND

Buckwheat (*Fagopyrum esculentum*) is a pseudocereal comprising high starch content (50-70% of starch in groat and flour), similar to the major cereal crops like rice, maize, and wheat. In addition to starch, significant amounts of protein (11-15%) are found in these seeds, and the proteins are of good quality. Indeed, the buckwheat is one of the best plant sources of protein of high functionalities and nutritional value. Concerning buckwheat fibers, the total quantity is comparable to those of cereal grains. Another advantage of buckwheat is the fact that it contains no gluten.

Thus, as a kind of healthy ingredient, food and pharmaceutical industries are looking for providing industrial methods to extract either the buckwheat proteins or the buckwheat starch, or even the buckwheat fibers depending on the desired applications.

CN101121756A discloses a method for extracting and refining starch from buckwheat groat. The fibers are removed through sieve, and then the starch is separated from proteins using hydrocyclone, and purified. Fibers and proteins are not valued in the process.

To the best knowledge of the Applicant, there is no prior art disclosing a method for extracting at the same time proteins, starch and fibers from buckwheat groat or flour and in which proteins are extracted during the first steps with the aim of not denaturing them.

So it is the merit of the Applicant to propose such an industrial method which presents the further advantages to be a simple, efficient and free of organic solvents and organic reactants.

Indeed all the steps of the process are performed only in presence of water and food-grade acids and bases, more particularly hydrochloric acid, sodium hydroxide and calcium hydroxide aqueous solutions.

There is no chemical transformation. Thus, the process proposed can be advantageously categorized as clean label process. The products obtained from the method according to the invention are therefore also clean label ingredients.

SUMMARY OF THE INVENTION

According to the present invention there is provided a process for extracting proteins, starch and fibers from a buckwheat flour or from a buckwheat groat, the process comprising the following steps of:

a) Preparing, at a temperature below 50° C., an aqueous suspension from the buckwheat flour or from the buckwheat groat with a pH between 7 and 9;
b) fractionating the aqueous suspension by density, so as to obtain a light fraction comprising proteins, soluble carbohydrates and salts, and a heavy fraction comprising starch and fibers;
c) treating the light fraction, so as to isolate the proteins;
d) treating the heavy fraction, so as to separate starch from fibers.

As used herein the expression "groat" refers to the hulled kernel of the buckwheat grain. Groat is the whole grain that includes a germ and fiber-rich bran portion of the grain as well as the endosperm. By definition, bran is the hard outer layers of the buckwheat grain which is particularly rich in fibers. The protein fraction extracted from the groat is mostly soluble. Endosperm is a tissue inside the buckwheat seed.

As used herein the expression "flour" refers to a powder made by grinding buckwheat grain. Most of the bran fraction can be removed by sieving.

DETAILED DESCRIPTION OF THE INVENTION

Step a) of the process according to the present invention consists of preparing, at a temperature below 50° C., an aqueous suspension from the buckwheat flour or from the buckwheat groat with a pH between 7 and 9.

In a preferred embodiment, the water is added to the buckwheat flour or to the buckwheat groat in a proportion 4:1 by weight. Such proportion allows the buckwheat flour to be homogeneously mixed into water and to form an aqueous suspension. The ratio is also suitable for the preparation of the aqueous suspension starting from buckwheat groat.

In order to avoid protein denaturation and starch gelatinization, it is essential to prepare the aqueous suspension at a temperature below 50° C.

Preferably the aqueous suspension is prepared at a temperature comprised between room temperature and 50° C.

Thus, according to a preferred embodiment of the present invention, the step a) of preparation of the aqueous suspension comprises a step of adding water to the buckwheat flour or to buckwheat groat in proportion of 4:1 (w/w) at a temperature comprised between room temperature and 50° C.

Further, when the process starts from a buckwheat groat, the step a) of preparation of the aqueous suspension comprises a step of wet grinding the whole buckwheat groat at a temperature below 50° C., preferably between room temperature and 50° C., for instance by using crude milling and/or colloid milling machine. Wet grinding advantageously prevents protein denaturation and enables to obtain the buckwheat aqueous suspension with the buckwheat particles in said suspension having an average particle size of 100 μm. Such particle size allows a further efficient extraction of the proteins, starch and fibers. Optionally, the buckwheat groat can be first cleaned by rinsing with cold water.

The aqueous suspension is then adjusted to a mild basic pH, at a pH comprised between 7 and 9, preferably at a pH comprised between 7.5 and 8.5. At this mild basic pH, buckwheat protein has higher solubility and the extraction of said proteins is thus facilitated. The pH is adjusted by means of diluted aqueous solution of sodium hydroxide or calcium hydroxide, such as at 1N concentration.

The aqueous suspension useful in the present invention comprises soluble compounds corresponding to proteins, soluble carbohydrates and salts, and insoluble compounds corresponding to fibers and starch.

Step b) of the process according to the present invention consists of fractioning by density at a pH between 7 and 9, preferably between 7.5 and 8.5, a light fraction comprising proteins, soluble carbohydrates and salts, and a heavy fraction comprising starch and fibers.

Thus, proteins are separated in the first steps of the process. That presents the advantage of not denaturing the proteins and of maintaining their functional and nutritional properties, but also better protein purity.

Step c) of the process according to the present invention consists of treating the light fraction so as to isolate the proteins, more particularly to obtain a fraction with 50-80% protein content.

The final proteins coming from buckwheat groat are mostly soluble unlike those coming from buckwheat flour, which have lower solubility. Indeed, the final proteins extracted from buckwheat flour comprise a part of insoluble proteins and another part of soluble proteins. Thus, the treating step of the light fraction of the buckwheat groat and the buckwheat flour is not exactly the same in order to obtain proteins, starch and fibers with good yield and high purity.

When the process starts from the buckwheat groat, the treating step comprises the following steps:
c1) adjusting the pH of the light fraction to the isoelectric pH of proteins at a temperature comprised between room temperature and 50° C., so as to precipitate the proteins;
c2) fractionating the light fraction by density, so as to separate the protein precipitate from a supernatant comprising most of soluble carbohydrates and salts;
c3) treating the protein precipitate at pH in the range of 6.5 to 7.5 at a temperature comprised between room temperature and 50° C., so as to neutralize and resolubilize the proteins;
c4) drying proteins.

In order to separate soluble carbohydrates and salts from proteins, the light fraction obtained from the ground buckwheat groat is adjusted to the isoelectric pH of proteins, corresponding to a pH comprised in the range of 4 to 5, preferably between 4 and 4.5. At this range of pH, proteins are in form of precipitate and most of soluble carbohydrates and salts remain soluble. The pH is adjusted by means of an aqueous solution of hydrochloric acid, 5% (v/v).

It is essential to treat the light fraction at a temperature below 50° C. in order to avoid protein denaturation, preferably at a temperature comprised between room temperature and 50° C. Thus, the separation of proteins from soluble carbohydrates and salts is particularly efficient.

A fractionating by density allows the separation of the soluble carbohydrates, salts and the protein precipitate, such as by using a conical plate centrifuge.

The protein precipitate thus isolated is treated at pH in the range of 6.5 to 7.5 to obtain a neutral aqueous solution in which the proteins are solubilized. To enhance the efficiency of the solubilization of proteins, the neutral aqueous solution comprising proteins is advantageously heated at a temperature below 50° C., preferably at a temperature comprised between room temperature and 50° C., in order to prevent protein denaturation.

The solubilized proteins are then dried. The drying step is carried out by using freeze dryer, vacuum oven dryer, drum dryer, or spray dryer, preferably by using spray dryer.

In the present invention, spray drying is used as a dehydration method which consists of spraying, in a chamber, a suspension of proteins in a stream of hot gas. The chamber comprises of, for this purpose, an inlet for heated gas, an outlet for discharging gas and an outlet for recovering the powder of dried proteins. This is the preferred method of drying of many thermally-sensitive materials such as proteins.

Advantageously, spray drying is a rapid, continuous, cost-effective, reproducible and scalable process for the production of dry powders from a fluid material by atomization through an atomizer into a hot drying gas medium, usually air.

Freeze drying, also known as lyophilisation, is a more expensive method used generally as an alternative on products that degrade in spray drying.

Optionally, the process of the present invention comprises a further step in which solubilized proteins are pasteurized before the drying step. For example, the pasteurization is performed in an UHT autoclave set, for instance by heating at 121° C. for 5 s then cooling down to 30° C.

In the present invention, when the process starts from buckwheat flour, the treating step of the light fraction comprises the following steps:
c'1) adjusting the pH of the light fraction to the isoelectric pH of proteins at a temperature comprised between room temperature and 50° C., so as to precipitate proteins;
c'2) fractionating the light fraction by density, so as to obtain a protein precipitate and a supernatant comprising soluble carbohydrates and salts;
c'3) treating the protein precipitate at pH in the range of 6.5 to 7.5 at a temperature comprised between room temperature and 50° C., so as to neutralize and partially resolubilize the proteins to obtain an insoluble protein fraction and a soluble protein fraction;
c'4) separating by filtration the insoluble protein fraction from the soluble protein fraction;
c'5) drying the insoluble proteins;
c'6) drying the soluble proteins.

In order to separate soluble carbohydrates and salts from proteins, the light fraction obtained from the buckwheat flour is adjusted to the isoelectric pH of proteins, corresponding to a pH comprised in the range of 4 to 5, preferably between 4 and 4.5. The pH is adjusted by means of an aqueous solution of hydrochloric acid, 5% (v/v). At this range of pH, soluble proteins and insoluble proteins are mostly in the form of precipitate, and most of the salts remain soluble. It is essential to treat the light fraction at a temperature below 50° C., preferably at a temperature comprised between room temperature and 50° C., in order to prevent protein denaturation. Thus, the separation of proteins from soluble carbohydrates and salts is particularly efficient.

A fractionating by density allows the separation of soluble the carbohydrates and salts from protein precipitate, such as by using a conical plate centrifuge. The protein precipitate thus isolated is then treated at pH in the range of 6.5 to 7.5 to obtain a neutral aqueous solution. At this range of pH, the soluble proteins are solubilized and the insoluble proteins are in the form of precipitate. To enhance the solubilization of the proteins, the neutral aqueous solution comprising proteins is heated at a temperature below 50° C., preferably at a temperature comprised between room temperature and 50° C., to prevent protein denaturation.

The proteins are then filtrated to separate the insoluble proteins (i.e. precipitate) from the soluble proteins (i.e. supernatant), separation by particle size.

The proteins are then dried. Preferably, the drying of the soluble proteins and insoluble proteins are carried out by using freeze dryer, vacuum oven dryer, drum dryer or spray dryer. More preferably, the insoluble proteins are dried by means of a vacuum oven dryer and the soluble proteins are spray dried.

Optionally, the process of the present invention comprises a further step in which solubilized proteins are pasteurized before the drying step. For example, the pasteurization is performed in an UHT autoclave set, for example by heating at 121° C. for 5 s then cooling down to 30° C.

Step d) of the process according to the present invention consists of treating the heavy fraction, so as to separate starch from fibers.

The treating step d) according to the present invention comprises the following steps of:
d1) adding water to the heavy fraction at a temperature comprised between room temperature and 50° C., so as to resuspend the heavy fraction and to obtain mixture of a fiber fraction and a starch fraction;
d2 separating by filtration the fiber fraction from the starch fraction at a temperature comprised between room temperature and 50° C.;
d3) drying the fibers;
d4 removing residual proteins in the starch fraction by density difference at pH 6-9 at a temperature comprised between room temperature and 50° C.;
d5 drying starch.

The heavy fraction is treated with water so as to form an aqueous suspension of starch and fibers, which will facilitate their separation by density and/or particle size, preferably by filtration. Two distinct fractions are therefore obtained: a fiber fraction and a starch fraction.

In a preferred embodiment, the separation is carried out by using sieve. Thus, fibers are retained on the sieve, and the starch particles pass through the sieve openings. For example; the sieve can be a vibration sieve, a rotary sieve or a curved sieve. Such sieves make easier the separation between starch and fibers.

The fibers thus isolated are then dried, and the starch fraction is retreated according to step d4) in order to remove any remaining proteins.

In a preferred embodiment, the treating step d4) of the starch fraction is repeated at least one time, more preferably three times. Advantageously, this step repetition allows increasing the purity of starch and increasing the yield of the protein fraction. The fractionation to remove the remaining proteins from the starch fraction or treating step of the starch fraction can be performed by means of centrifuge or hydrocyclone.

The starch fraction thus obtained is then dried.

In a preferred embodiment of the process according to the present invention, the drying steps d3) and d5) of the treating step of the heavy fraction are carried out by using fluidized bed dryer, freeze dryer or hot air dryer.

Optionally, the pH of starch fraction can be adjusted to pH 5.5-7 prior to drying.

In a preferred embodiment of the process according to the present invention, all the fractionating steps by density (steps b), c2), c'2) and d4)) include a mechanical separating step, such as decantation or centrifugation. For example, the mechanical separating step is carried out by using a horizontal screw decanter, a centrifugal decanter or a hydrocyclone.

In a preferred embodiment of the process according to the present invention, all the separating steps by filtration (steps c'4) and d2)) are carried out by using sieve having mesh size comprised between 100 to 125 µm, which is suitable to separate the particles based on their different sizes.

In a preferred embodiment of the process according to the present invention, the temperature of the steps a), c), d) is strictly below 50° C. in order to prevent buckwheat protein denaturation and buckwheat starch gelatinization. More preferably, the temperature of the steps a), c), d) is comprised between room temperature and 50° C. It is advantageous to work at a temperature approaching 50° C. to efficiently solubilize the proteins. A further advantage to work at a temperature approaching 50° C. is the fact that microbial growth is reduced.

In the process according to the present invention, no ultrasonication step is used. The main reason is the fact that ultrasonication may damage the starch granules and denature the proteins.

Another object of the present invention is buckwheat proteins obtained by the process according to the present invention.

Buckwheat proteins obtained by the process of the invention have a yield comprised between 2 and 10% from the buckwheat groat or the buckwheat flour, and a purity in the range of 50 to 80%.

Buckwheat proteins obtained by the process of the invention present the advantage not to be denatured during the process of the present invention. Thus, their functionalities, such as solubility, are maintained along with good sensory attributes and high nutritional value. The process only uses water and food-grade acids and bases, no chemical solvents. Therefore the proteins obtained can be qualified as clean label ingredients and can be used in many applications, such as food and beverage applications, mainly as a source of healthy, gluten-free plant-based proteins.

Still another object of the present invention is the buckwheat starch obtained by the process of present invention.

Buckwheat starch obtained by the process of the invention has a yield comprised between 45 and 60% from the buckwheat groat or the buckwheat flour and a purity superior to 90%, preferably between 95% and 100%.

Buckwheat starch obtained by the process of the invention presents the advantage not to be gelatinized during the process of the present invention.

Thus, the non-gelatinized buckwheat starch maintains its original physicochemical properties, including good shear and heat resistances. They can be used in many applications, such as clean label native starch to replace cross-linked modified starches.

One further object of the present invention is the buckwheat fibers obtained by the process of the present invention.

Buckwheat fibers obtained by the process of the invention have a yield less than 35% from the buckwheat groat or the buckwheat flour. The fibers have the potentials for increasing fiber content in foods, such as in bakery products and pastas. Due to the presence of residual starch and proteins, the fibers also have some functionalities useful for some food applications, such as for binding agent and thickening agent.

Other characteristic and advantages of the present invention will appear clearly on reading the examples given below which illustrates the invention without however limiting it.

EXAMPLES

Example 1

Common buckwheat groat (400 g) is mixed with water in a proportion of 1:4 (w/w.) at 45° C. Then it is milled in a blender for 5 min to produce an aqueous suspension. The pH of the aqueous suspension is adjusted to 8 at 45° C. by means of an aqueous solution of sodium hydroxide, 1N, so as to enhance the solubilization of proteins. The proteins in the aqueous suspension allowed to solubilize by means of mechanical stirring for 1 hour.

The aqueous suspension is then introduced into a lab centrifuge at 1700 g for 10 minutes at room temperature. The centrifugation leads to the production of two fractions: a first fraction (i.e. supernatant) rich in proteins, soluble carbohydrates and salts and a second fraction (i.e. precipitate) comprising starch and fibers.

The pH of the first fraction is adjusted to pH 4.5 (isoelectric point) by adding hydrochloric acid, 5% (v/v) at 45° C., so as to precipitate the proteins. The separation of the protein fraction (i.e. precipitate) from soluble carbohydrates and salts (i.e. supernatant) is performed by means of a lab centrifuge at 760 g for 5 minutes at room temperature. The protein fraction (i.e. precipitate) thus obtained is neutralized at pH 7 with an aqueous solution sodium hydroxide, 1N at room temperature, so as to re-solubilize the protein fraction. The concentrated protein fraction is then dried by spray drying for 2 hours. The protein fraction is obtained with a yield of 6.6% from the buckwheat groat and has a purity of 75%.

The second fraction (i.e. precipitate) comprising the starch and fiber mixture is treated with water at room temperature and passed through a sieve of 120 mesh (125 µm), so as to obtain a fraction rich in fibers and a fraction rich in starch. Then, the fiber fraction is washed with water, so as to remove residual starch.

The fiber fraction is dried using a fluidized bed dryer. The fiber fraction is obtained with a yield of 22% and has purity of 16% cellulose.

So as to remove residual proteins of the starch fraction, the starch fraction is first treated at pH 8 by means of aqueous solution of sodium hydroxide, 1N at room temperature, then after 1 hour of mechanical stirring at room temperature. It is introduced into a centrifuge at 1700 g for 10 minutes at room temperature. A small protein fraction is obtained as supernatant and a starch fraction as precipitate. This operation is repeated 3 times for removing all the residual proteins. Then, the starch fraction is readjusted at pH 7 and dried using a fluidized bed dryer. The starch fraction is obtained with a yield of 50% from the ground buckwheat groat and has a purity of 95%.

Example 2

Common buckwheat flour (400 g) is suspended in water in a proportion of 1:4 (w/w), and homogeneously mixed by means of mechanical stirring in order to form an aqueous suspension. The pH of the aqueous suspension is adjusted to 8 at 45° C. by means of an aqueous solution of sodium hydroxide, 1N, so as to enhance the solubilization of proteins. The proteins in the aqueous suspension are allowed to solubilize by means of mechanical stirring for 1 hour.

The aqueous suspension is then introduced into a lab centrifuge at 1700 g for 10 minutes at room temperature. The centrifugation leads to the production of two fractions: a first fraction (i.e. supernatant) rich in proteins, soluble carbohydrates and salts and a second fraction (i.e. precipitate) comprising the starch and fiber mixture.

The pH of the first fraction is adjusted to pH 4.5 (isoelectric point) by adding an aqueous solution of hydrochloric acid, 5% (v/v) at 45° C., so as to precipitate the proteins. The separation of the protein fraction (i.e. precipitate) from the soluble carbohydrates and salts (i.e. supernatant) is performed by means of a lab centrifuge at 760 g for 5 minutes at room temperature. The protein fraction (i.e. precipitate) thus obtained is neutralized at pH 7 by means of an aqueous solution of sodium hydroxide, 1N at room temperature and then is passed through a sieve of 120 mesh (125 µm), so as to obtain a fraction of insoluble proteins and a fraction of soluble proteins. The soluble protein fraction is dried by spray drying for 2 hours and the insoluble protein fraction is dried by vacuum oven drying for 8 hours.

The soluble protein fraction is obtained with a yield of 3% from the buckwheat flour and has a purity of 74%. The insoluble protein fraction is obtained with a yield of 3% from the buckwheat flour.

The second fraction (i.e. precipitate) comprising the starch and fiber mixture is treated with water at room temperature and passed through a sieve of 120 mesh (125 µm), so as to obtain a fraction rich in fibers and a fraction rich in starch. Then, the fiber fraction is washed with water, so as to remove residual starch.

The fiber fraction is dried using a fluidized bed dryer. The fiber fraction is obtained with a yield of 32% and has purity of 10% cellulose.

So as to remove residual proteins of the starch fraction, the starch fraction is first treated at pH 8 by means of an aqueous solution of sodium hydroxide, 1N at room temperature, then after 1 hour of mechanical stirring at room temperature. It is introduced into a lab centrifuge at 1700 g for 10 minutes at room temperature. A small protein fraction is obtained as supernatant and a starch fraction as precipitate. This operation is repeated 3 times for removing all the residual proteins. Then, the starch fraction is readjusted at pH 7 and dried using a fluidized bed dryer. The starch fraction is obtained with a yield of 50% from the buckwheat flour and has a purity of 95%.

Example 3

Buckwheat groat (100 kg) is mixed with water in a proportion of 1:4 (w/w.) at 45° C. Then it is milled in a crude miller then colloid miller until reaching an average particle size of 100 µm. The pH of the aqueous suspension is adjusted to 8 at 45° C. by means of an aqueous solution of sodium hydroxide, 1N, so as to enhance the solubilization of proteins. The proteins in the aqueous suspension are allowed to solubilize by means of mechanical stirring for at least 1 hour. The aqueous suspension is then introduced into a horizontal decanter at 3500 g at room temperature. The centrifugation leads to the production of two fractions: a first fraction (i.e. supernatant) rich in proteins, soluble carbohydrates, salts and second fraction (i.e. a precipitate) comprising starch and fibers.

The pH of the first fraction is adjusted to pH 4.5 (isoelectric point) by adding hydrochloric acid, 5% (v/v) at 45° C. to the first fraction, so as to precipitate the proteins. The separation of the protein fraction (i.e. precipitate) from soluble carbohydrates and salts (i.e. supernatant) is performed by means of a conical plate centrifuge at 9500 g at room temperature. The protein fraction (i.e. precipitate) thus obtained is neutralized at pH 7 with an aqueous solution of sodium hydroxide, 1N at room temperature, so as to resolubilize the protein fraction. The concentrated protein fraction is then dried by spray drying for 2 hours with inlet temperature 170° C. and outlet temperature 105° C.

The protein fraction is obtained with a yield of 2% from the buckwheat groat and has a purity of 65%.

The second fraction (i.e. precipitate) comprising the starch and fiber mixture is treated with water at room temperature and passed through a sieve of 150 mesh, so as to obtain a fraction rich in fibers and a fraction rich in starch.

The fiber fraction is dried using a hot air dryer. The fiber fraction is obtained with a yield of 12% and has purity of 10% total fiber.

So as to remove residual proteins of the starch fraction, the starch fraction is purified with hydrocyclone. A small protein fraction is obtained as light phase and a starch fraction as heavy phase. Then, the starch fraction is dried using a plate filter and fluidized bed dryer.

The starch fraction is obtained with a yield of 50% from the ground buckwheat groat and has a purity of 92%.

The invention claimed is:

1. A process for extracting buckwheat proteins, buckwheat starch and buckwheat fibers from a buckwheat flour or from a buckwheat groat, said buckwheat being common buckwheat (*Fagopyrum esculentum*), the process being free of organic solvents and organic reactants and comprising the steps of:
   a) preparing an aqueous suspension from the buckwheat flour or from the buckwheat groat with a pH between 7 and 9, wherein the preparation of the aqueous suspension comprises a step of adding water to the buckwheat flour or to buckwheat groat in proportion of 4:1 (w/w) at a temperature comprised between room temperature and 50° C.,
   b) fractionating the aqueous suspension by density, so as to obtain a light fraction (supernatant) comprising proteins, soluble carbohydrates and salts, and a heavy fraction (precipitate) comprising starch and fibers;
   c) treating the light fraction (supernatant), so as to isolate the proteins; and
   d) treating the heavy fraction (precipitate), so as to separate starch from fibers;
   wherein when the process starts from buckwheat groat the step a) of preparation of the aqueous suspension comprises a step of wet grinding to obtain the buckwheat aqueous suspension with the buckwheat particles in said suspension having an average particle size of 100 μm, wherein when the process starts from buckwheat groat, the treating step of the light fraction c) comprises the following steps:
   c1) adjusting the pH of the light fraction to the isoelectric pH of proteins, corresponding to a pH comprised in the range of 4 to 5, at a temperature comprised between room temperature and 50° C., so as to precipitate proteins;
   c2) fractionating the light fraction by density, so as to separate the protein precipitate from a supernatant comprising soluble carbohydrates and salts;
   c3) treating the protein precipitate at pH in the range of 6.5 to 7.5 at a temperature comprised between room temperature and 50° C., so as to neutralized and resolubilize proteins; and
   c4) drying said proteins
      wherein, when the process starts from buckwheat flour, the treating step of the light fraction c) comprises the following steps:
   c'1) adjusting the pH of the light fraction to the isoelectric pH of proteins, corresponding to a pH comprised in the range of 4 to 5, at a temperature comprised between room temperature and 50° C., so as to precipitate proteins;
   c'2) fractionating the light fraction by density, so as to obtain a protein precipitate and a supernatant comprising soluble carbohydrates and salts;
   c'3) treating the protein precipitate at pH in the range of 6.5 to 7.5 at a temperature comprised between room temperature and 50° C., so as to neutralize and partially resolubilize the proteins to obtain an insoluble protein fraction and a soluble protein fraction;
   c'4) separating by filtration the insoluble protein fraction from the soluble protein fraction;
   c'5) drying the insoluble proteins; and
   c'6) drying the soluble proteins,
   wherein yield of buckwheat protein from said process is 2 to 10%, yield of buckwheat starch from said process is 45 to 60% and yield of buckwheat fiber from said process is less than 35%.

2. The process according to claim 1, wherein the process is free of organic solvents and free of organic reactants.

3. The process according to claim 1, wherein the treating step d) of the heavy fraction comprises the following steps:
   d1) adding water to the heavy fraction at a temperature comprised between room temperature and 50° C., so as to resuspend the heavy fraction and to obtain a fiber fraction and a starch fraction;
   d2) separating the fiber fraction from the starch fraction based at a temperature comprised between room temperature and 50° C.;
   d3) drying the fibers;
   d4) removing residual proteins in the starch fraction by density difference at pH 6-9 at a temperature comprised between room temperature and 50° C.; and
   d5) drying the starch fraction.

4. The process according to claim 3, wherein the treating step d4) of the starch fraction is repeated at least one time.

5. The process according to claim 3, wherein the drying steps d3) and d5) of the treating step of the heavy fraction are carried out by using fluidized bed dryer, freeze dryer or hot air dryer.

6. The process according to claim 1, wherein the drying steps c4), c'5) and c'6) of the treating step of the light fraction are carried out by using vacuum oven dryer, freeze dryer, or spray dryer.

7. The process according to claim 1, wherein the separating steps (steps c'4) and d2)) by filtration are carried out by using sieve having size comprised between 100 and 125 μm.

8. The process according to claim 1, wherein the fractionating step by density (steps b), c2), c'2) and d4)) includes a mechanical fractionating step, the mechanical fractionating step being carried out by using a horizontal screw decanter, a centrifugal decanter or a hydrocyclone.

9. The process according to claim 1, wherein when the process starts from buckwheat groat, the treating step of the light fraction c1) comprises adjusting the pH of the light fraction to a pH value of 4.5 at a temperature comprised between room temperature and 50° C., so as to precipitate the proteins.

10. The process according to claim 1, wherein when the process starts from buckwheat flour, the treating step of the light fraction c'1) comprises adjusting the pH of the light fraction to a pH value of 4.5 at a temperature comprised between room temperature and 50° C., so as to precipitate the proteins.

* * * * *